(12) United States Patent
Ma et al.

(10) Patent No.: US 9,125,940 B2
(45) Date of Patent: Sep. 8, 2015

(54) COMPOSITIONS AND METHODS FOR TREATING MACULAR EDEMA

(76) Inventors: Zhuning Ma, Sunnyvale, CA (US); Jingran Chen, Sunnyvale, CA (US)

( * ) Notice: Subject to any disclaimer, the term of this patent is extended or adjusted under 35 U.S.C. 154(b) by 0 days.

(21) Appl. No.: 13/365,160

(22) Filed: Feb. 2, 2012

(65) Prior Publication Data

US 2012/0201830 A1 Aug. 9, 2012

Related U.S. Application Data

(60) Provisional application No. 61/439,152, filed on Feb. 3, 2011.

(51) Int. Cl.

| | |
|---|---|
| *A61K 31/385* | (2006.01) |
| *A61K 31/353* | (2006.01) |
| *A61K 31/202* | (2006.01) |
| *A61K 31/122* | (2006.01) |
| *A61K 31/07* | (2006.01) |
| *A61K 31/355* | (2006.01) |
| *A61K 31/375* | (2006.01) |
| *A61K 31/593* | (2006.01) |
| *A61K 33/30* | (2006.01) |
| *A61K 33/06* | (2006.01) |
| *A61K 45/06* | (2006.01) |
| *A61K 31/232* | (2006.01) |

(52) U.S. Cl.
CPC ............... *A61K 45/06* (2013.01); *A61K 31/07* (2013.01); *A61K 31/122* (2013.01); *A61K 31/202* (2013.01); *A61K 31/232* (2013.01); *A61K 31/353* (2013.01); *A61K 31/355* (2013.01); *A61K 31/375* (2013.01); *A61K 31/385* (2013.01); *A61K 31/593* (2013.01); *A61K 33/06* (2013.01); *A61K 33/30* (2013.01)

(58) Field of Classification Search
CPC . A61K 31/385; A61K 31/353; A61K 31/202; A61K 31/122
See application file for complete search history.

(56) References Cited

U.S. PATENT DOCUMENTS

| | | | | |
|---|---|---|---|---|
| 6,329,432 | B2 * | 12/2001 | Howard et al. | 514/725 |
| 6,660,297 | B2 * | 12/2003 | Bartels et al. | 424/464 |
| 7,282,225 | B1 | 10/2007 | Davis et al. | |
| 2001/0031744 | A1 * | 10/2001 | Kosbab | 514/54 |
| 2008/0038316 | A1 * | 2/2008 | Wong et al. | 424/426 |
| 2008/0312128 | A1 | 12/2008 | Chaum et al. | |
| 2009/0226547 | A1 * | 9/2009 | Gilbard et al. | 424/729 |
| 2010/0233145 | A1 | 9/2010 | van Veen | |

OTHER PUBLICATIONS

Artwohl, M. et al. (2007) "R-(+)-α-lipoic acid inhibits endothelial cell apoptosis and proliferation: involvement of Akt and retinoblastoma protein/E2F-1," Am J Physiol Endocrinol Metab 293:E681-E689.
Chen, W. et al. (2005) "Anti-inflammatory Effect of Docosahexaenoic Acid on Cytokine-Induced Adhesion Molecule Expression in Human Retinal Vasular Endothelial Cells," Invest Ophthalmol Vis Sci 46(11):4342-4347.
Delcourt, C. et al. (2010) "Nutrition and Age-Related Eye Diseases: The ALIENOR (Antioxydants, Lipides Essentiels, Nutrition et Maladies OculaiRes) Study," J Nutr Health Aging 14(10):854-861.
Gao, L. et al. (2012) "Effects of coenzyme Q10 on vasular endothelial function in humans: A meta-analysis of randomized controlled trials," Atherosclerosis 221:311-316.
Golbidi, S. et al. (2011) "Diabetes and alpha lipoic acid," Frontiers in Pharmacology 2(69):1-15.
Larghero, P. et al. (2007) "Biological assays and genomic analysis revel lipoic acid and modulation of endothelial cell behavior and gene expression," Carcinogenesis 28(5):1008-1020.
Matesanz, M. et al. (2010) "Docosahexaenoic Acid Improves the Nitroso-Redox Balance and Reduces VEGF-Mediated Angiogenic Signalling in Microvascular Endothelial Cells," Invest Ophthalmol Vis Sci. 51:6815-6825.
Qu, J. et al. (2009) "Coenzyme Q10 in the Human Retina," Investigative Ophthalmology & Visual Science 50(4):1814-1818.
Salinthone, S. et al. (2010) "Lipoic Acid Attenuates Inflammation via cAMP and Protein Kinase A Signalling," PLoS One 5(9) e13058:1-10.
Voloboueva, L.A. (2005) "(R)-α-Lipoic Acid Protects Retinal Pigment Epithelial Cells from Oxidative Damage," Invest Ophthalmol Vis Sci. 46(11):4302-4310.

* cited by examiner

*Primary Examiner* — Jonathan S Lau
(74) *Attorney, Agent, or Firm* — VLP Law Group LLP; Dianne E. Reed

(57) ABSTRACT

Provided are compositions and methods for the treatment of macular edema, in particular that results from central retinal vein occlusion (CRVO), branch retinal vein occlusion (BRVO), age related macular degeneration (AMD), diabetes, or eye surgical procedures. The composition strengthens retinal health through the prevention, stabilization and/or treatment of macular edema. The composition can include polyphenolic compounds extracted from natural plants, an alpha lipoic acid, docosahexaenoic acid (DHA) and/or eicosapentaenoic acid (EPA), and ubiquinone.

19 Claims, 2 Drawing Sheets

COMPOSITIONS AND METHODS FOR TREATING MACULAR EDEMA

CROSS REFERENCE TO RELATED APPLICATIONS

This application claims the benefit under 35 U.S.C. §119(e) of U.S. Provisional Application Ser. No. 61/439,152 filed Feb. 3, 2011, the content of which is incorporated by reference in its entirety.

FIELD OF THE INVENTION

The present disclosure generally relates to compositions and methods for the prevention, stabilization and/or treatment of macular edema, in particular that results from central retinal vein occlusion (CRVO), branch retinal vein occlusion (BRVO), age related macular degeneration (AMD), diabetes in adult particularly the elderly, or eye surgical procedures.

BACKGROUND

The leading causes of vision impairment (e.g., low vision and blindness) in older Americans include macular degeneration, glaucoma, cataract and diabetic retinopathy. Age-related visual impairment is second only to arthritis/rheumatism as a cause of disability. Vision loss ranks third below arthritis and heart disease as a top cause of impaired daily functioning in people over the age of 70. The projections are that, by 2020, as many as 5.5 million Americans will suffer from low vision or blindness.

Macular edema occurs when fluid and protein deposits collect on or under the macula of the eye, causing it to thicken and swell. It contributes to vision loss by altering the functional cell relationship in the retina and promoting an inflammatory reparative response. Macular edema may be intracellular or extracellular. Extracellular accumulation of fluid, which is more frequent and clinically more relevant, is directly associated with an alteration of the blood-retinal barrier (BRB).

Macular edema may be caused by retinal vein occlusions (RVOs). RVOs are known as retinal vascular disorders characterized by engorgement and dilatation of the retinal veins with secondary, mostly intraretinal hemorrhages and mostly intraretinal (and partially subretinal) edema, retinal ischemia, and macular edema. RVOs include central retinal vein occlusion (CRVO) and branch retinal vein occlusion (BRVO).

Various approaches have been documented in attempting to manage CRVO. Grid laser treatment has shown poor efficacy in treating CRVO. Intravitreal injection of steroids led to several undesirable side effects such as cataract or secondary ocular hypertension. Intravitreal injection of anti-VEGF agents has shown promises in treating macular edema of different origins. However, such intervention is considered invasive. Furthermore, patients may need regular injections. In many cases, moreover, they need to continue to receive such treatments for the rest of their lives.

Diabetic macular edema (DME), a retinal thickening involving the center of the macula, represents the most common cause of vision loss in patients affected by diabetes mellitus. DME occurs in approximately 14% of diabetics. The incidence of diabetic macular edema is closely associated with the degree of diabetic retinopathy and the duration and type of the disease. Diabetic retinopathy results from the inner blood-retinal barrier being compromised, which leads to leakage of plasma constituents in the surrounding retina. Vision loss due to diabetic retinopathy may result from several mechanisms. Macular edema or capillary nonperfusion may directly impair central vision.

Fewer than 10% type II diabetic patients have DME five years after the diagnosis of diabetes, while close to 30% suffer from DME 20 years after the diagnosis. For type I diabetic patients the incident of DME is low in the first five years but is close to 30% 20 years after the diagnosis. Patients treated with insulin have a higher risk of developing macular edema. Photocoagulation is the standard of care for diabetic macular edema. However, many patients are unresponsive to laser therapy and fail to improve after photocoagulation. Current interventions also include the intravitreal administration of steroids. However it may lead to a significant increase in intraocular pressure.

Patients with diabetic macular edema have been found to have increased levels of VEGF in the vitreous. Thus, potent and specific anti-VEGF drugs have become common treatment of diabetic macular edema. On the other hand, the frequent injections for a presumably extended period that may be required with the currently available anti-VEGF drugs, make injection-related complications such as infectious endophthalmitis a drawback.

Age-related macular degeneration (AMD) is the leading cause of central blindness or low vision among the elderly in industrialized countries. In the US alone, there are close to 10 million patients suffering from AMD, close to 2 million have advanced AMD, which is also called wet AMD. The other form of AMD is called dry AMD, which is an early stage of the disease and may result from the aging and thinning of macular tissues, depositing pigment in the macula, or a combination of the two processes.

For generalized health problems such as diabetes or high blood pressure, it is evident that systemic medical therapy should be considered first and foremost. However, systemic approach has fallen to the sideline when it comes to treating retinal disorders. This is simply due to their poor bioavailability in retina when products are taken systemically. In addition, in order to have a therapeutic level of product in retina, higher dose must be taken which may lead to systemic toxicity.

SUMMARY

The present disclosure, in one embodiment, provides a composition comprising an effective amount of each of (a) a polyphenolic compound, (b) an alpha lipoic acid, a dihydrolipoic acid, or a salt or amide thereof, (c) docosahexaenoic acid (DHA) or an ethyl ester thereof and/or eicosapentaenoic acid (EPA) or an ethyl ester thereof, and (d) ubiquinone or ubiquinol.

In one aspect, the polyphenolic compound is one or more proanthocyanidin. In another aspect, the composition further comprises a vitamin selected from vitamin A, vitamin B, vitamin C, vitamin D, vitamin E, or combinations thereof. In yet another aspect, the composition further comprises a mineral, such as, zinc, magnesium, an oxide or a salt thereof, or combinations thereof. In some aspects, the composition further comprises a pharmaceutically acceptable carrier.

In one embodiment, the composition comprises about 25-800 mg proanthocyanidin, about 25-1800 mg alpha lipoic acid, about 100-2000 mg DHA and EPA combined, and about 20-1000 mg ubiquinone. In another embodiment, the composition comprises about 30-200 mg proanthocyanidin, about 30-400 mg alpha lipoic acid, about 500-1500 mg DHA and EPA combined, and about 50-300 mg ubiquinone.

In some aspect, the composition is presented in a tablet, a capsule, or a liquid.

Another embodiment of the present disclosure provides a composition consisting essentially of an effective amount of each of (a) a polyphenolic compound, (b) an alpha lipoic acid, a dihydrolipoic acid, or a salt or amide thereof, (c) docosahexaenoic acid (DHA) or an ethyl ester thereof, and/or eicosapentaenoic acid (EPA) or an ethyl ester thereof, and (d) ubiquinone or ubiquinol. In one aspect, the composition further comprises one or more selected from vitamin A, vitamin B, vitamin C, vitamin D, vitamin E, zinc or magnesium in an oxide or a salt form, or combinations thereof.

Methods of treatment are also provided. In one embodiment, provided is a method of improving the vision acuity of a macular edema patient, comprising administering to patient an effective amount of a composition of the present disclosure.

Another embodiment provides a method of treating macular edema in a patient in need thereof, comprising administering to the patient a therapeutically effective amount of a composition of the present disclosure. In one aspect, the macular edema patient has suffered or suffers from diabetes, a retinal vascular disorder or an eye surgical procedure. In another aspect, the retinal vascular disorder comprises central retinal vein occlusion (CRVO), branch retinal vein occlusion (BRVO), age related macular degeneration (AMD), glaucoma, or combinations thereof.

Administration can be oral, intravitreal, topical, intravenous, parenteral, intraperitoneal, sublingual, or bucal, without limitation.

For the treatment methods, in one aspect, the administration comprises a daily dose of about 30-200 mg proanthocyanidin, about 30-400 mg alpha lipoic acid, about 500-1500 mg DHA and EPA combined, and about 50-300 mg ubiquinone.

In some aspects, the methods further comprise administering to the patient a therapeutically effective amount of an anti-inflammatory agent. In some aspects, the anti-inflammatory agent is a nonsteroidal anti-inflammatory drug (NSAID). In some aspects, the anti-inflammatory agent is a steroid. In some aspects, the pro-drug of the anti-inflammatory agent is administering to the patient. In some aspects, the anti-inflammatory agent is administered orally, intravitreally, topically as an eye drop, as a cream, or in a transdermal patch, or through transcorneal or transsclera/conjunctival route.

In one aspect, the methods further comprise administering to the patient an anti-VEGF antibody. In one aspect, the methods further comprise administering to the patient a carbonic anhydrase inhibitor or its pro-drug. In one aspect, the methods further comprise administering to the patient an immunosuppressive agent or its pro-drug. In still one aspect, the methods comprise treating the patient with an eye surgical procedure, for example, laser photocoagulation or with photodynamic therapy.

DETAILED DESCRIPTION

Figure 1:
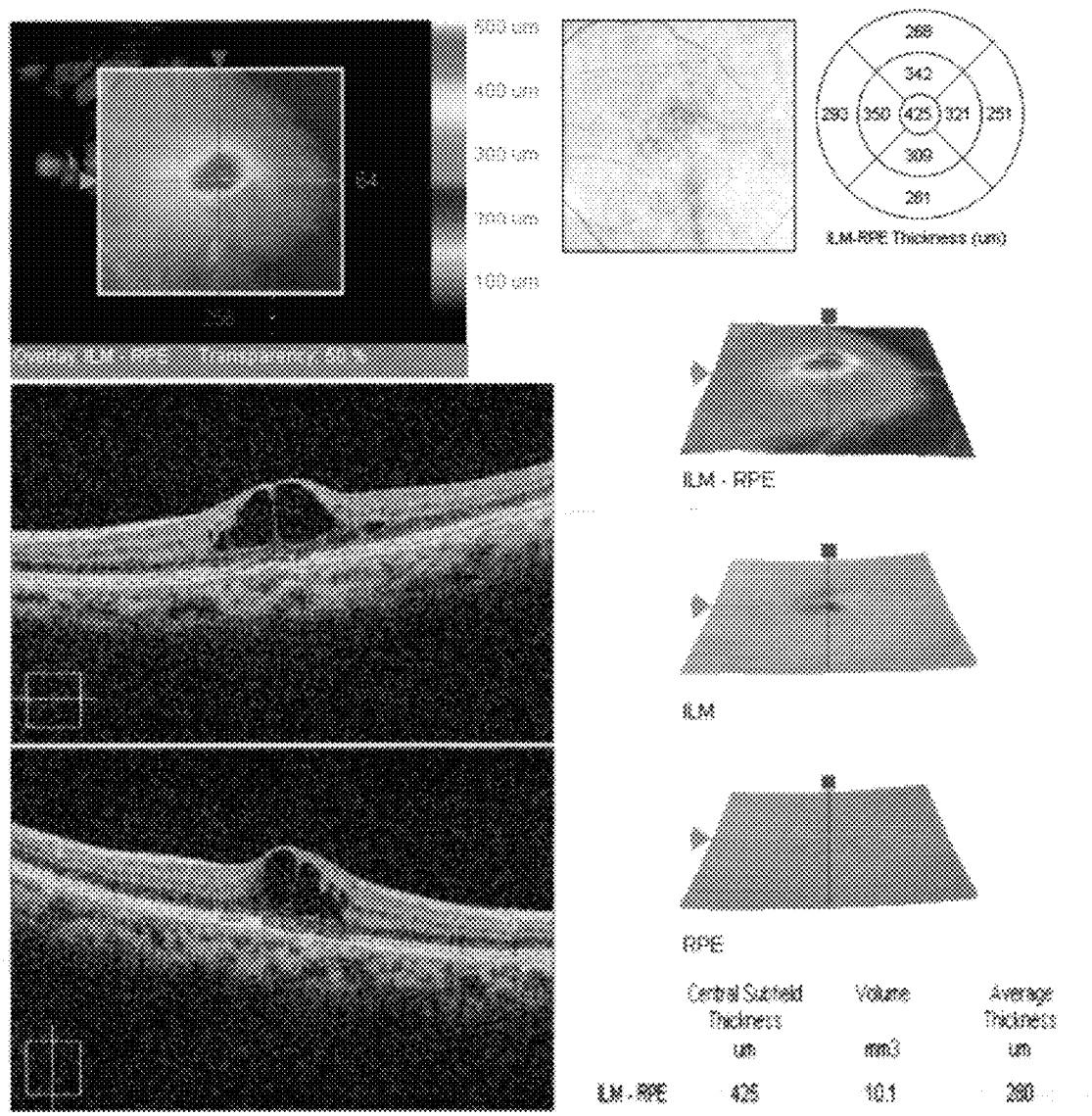
FIG. 1 includes Optical Coherence Tomography (OCT) images showing macular edema in the left eye of the patient, before being treated with the present technology, in Example 1. The pictures were taken in June 2008, three months after Avastin injection. The vision acuity was 20/40 and the ocular pressure was 35 mmHg.

The present disclosure provides data to demonstrate that the disclosed compositions are effective in treating macular edema in patients, and in treating associated symptoms and conditions.

DEFINITIONS

An "effective amount" is an amount sufficient to achieve beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present disclosure for any particular subject depends upon a variety of factors including the activity of the specific composition employed, bioavailability of the composition, the route of administration, the age of the patient and its body weight, general health, gender, the diet of the patient, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. Studies in animal models generally may be used for guidance regarding effective dosages for treatment of diseases. These considerations, as well as effective formulations and administration procedures are well known in the art and are described in standard textbooks. Consistent with this definition and as used herein, the term "therapeutically effective amount" is an amount sufficient to treat a specified disorder or disease or alternatively to obtain a pharmacological response.

The term "administration" shall include without limitation, administration by ocular, oral, parenteral (e.g., intramuscular, intraperitoneal, inhalation, transdermal intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, ocular etc.) and can be formulated, alone or together, in suitable dosage unit formulations containing conventional non-toxic pharmaceutically acceptable carriers, adjuvants, excipients, and vehicles appropriate for each route of administration. The disclosure is not limited by the route of administration, the formulation or dosing schedule.

As used herein, "treating" or "treatment" of a disease in a patient refers to (1) preventing the symptoms or disease from occurring in an animal that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this disclosure, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In one aspect, treating macular edema in a patient comprises improving the vision acuity of the patient. In another aspect, treating macular edema in a patient comprises maintaining the intraocular pressure in the patient. In yet another aspect, treating macular edema in a patient comprises treating glaucoma associated with CRVO. In still another aspect, treating macular edema in a patient comprises slowing down the macular degeneration process in the patient.

DETAILED DESCRIPTION

Macular edema can result from an accumulation of fluid in the retinal layers around the fovea. It contributes to vision loss by altering the functional cell relationship in the retina and promoting an inflammatory reparative response. Macular edema is clinically relevant type of macular response to an altered retinal environment. In most cases, it is associated with an alteration of the blood-retinal barrier (BRB). When macular edema persists for more than six months, it is considered as chronic macular edema and treatment if required.

It is herein discovered, that the combination of four clinically proved safe ingredients: (1) polyphenolic compounds such as proanthocyanidin, (2) alpha lipoic acid, (3) ubiquinone, and (4) omega-3 fatty acids including docosahexaenoic acid (DHA) and eicosapentaenoic acid (EPA), are effective in treating macular edema. It is contemplated that each of these ingredients brings its unique benefits, and when used together, they reduce vascular permeability, protect epithelial and endothelial cells, enhance microcirculation, and attenuate adverse effects of vascular endothelial growth factors. Furthermore, when taken orally, they also help to reduce hypertension and hyperglycemia systemically.

Alpha lipoic acid (ALA), as well as its reduced form, dihydrolipoic acid (DHLA), can attenuate vascular hyperpermeability, reactive oxygen spieces (ROS) formation and cytochrome C formation. As a potent antioxidant, it can protect epithelial and endothelial cells against oxidative stress. They are fat and water soluble and can enter the blood-retinal barrier. Their bioavailability in retina, it is observed, can reach a therapeutic level when taken orally.

Polyphenolic compounds such as catechin, epicatechin, and procyanidins can enhance microcirculation and reduce levels of microangiopathy, particularly associated with diabetes.

Omega-3 fatty acids, on the other hand, protect retina based on their anti-angiogenic properties. Omega-3 fatty acids can reduce VEGF mediated angiogenesis and maintain vascular integrity. The combination of omega-3 fatty acids and alpha lipoic acid appears to exhibit synergistic anti-VEGF effects.

Ubiquinone or co-enzyme Q10 is normally present in human retina and the level may decrease with age. It has been shown when combined with omega-3 fatty acids and acetyl-L-carnitine, ubiquinone can be useful for treating early age-related macular degeneration through improving mitochondrial dysfunction. The present inventors discovered, however, the combination of ubiquinone and omega-fatty acid along with alpha lipoic acid and procyanidins, without L-carnitine, can achieve the same or even better result.

Compositions

Thus, one embodiment of the present disclosure provides a composition comprising an effective amount of each of (a) a polyphenolic compound particularly those extracted from natural plants, (b) an alpha lipoic acid, a dihydrolipoic acid, or a salt or amide thereof, (c) docosahexaenoic acid (DHA) or an ethyl ester thereof and/or eicosapentaenoic acid (EPA) or an ethyl ester thereof, and (d) ubiquinone or ubiquinol.

In one aspect, "polyphenolic compounds" as used here, refer to compounds having at least two phenolic structural units. Polyphenols are compounds well known in the art and can be prepared either synthetically or by purification and modification from the natural environment. In the present disclosure, the polyphenols are particularly from natural origins. Without limitation, polyphenols include hydrolyzable tannins (gallic acid esters of glucose and other sugars or cyclitols) and phenylpropanoids, such as lignins, flavonoids, condensed tannins, and phenolic acids. Polyphenolic compounds, such as proanthocyanidins, are anti-oxidants.

Without limitation, flavonoids include flavanols (or flavan-3-ols), flavones, anthocyanidins, isoflavonoids, and neoflavoids. In a particular aspect, the flavonols are proanthocyanidins.

"Proanthocyanidins", also known as "Oligomeric proanthocyanidins" or "OPCs" refers to procyanidins, prodelphinidins and propelargonidins, in particular flavan-3-ols (for example, catechin, epicatechin and/or their oligomers), and flavones (for example, taxifolin). The structure of epicatechin is shown below:

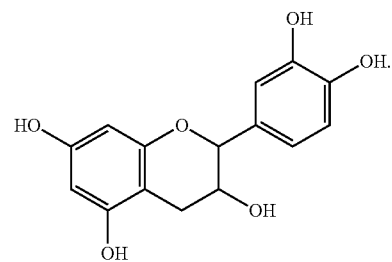 [SMILES: Oc1cc(O)c2c(c1)OC(c1ccc(O)c(O)c1)C(O)C2]

Catechin, referring to (2R,3S)-2-(3,4-dihydroxyphenyl)-3,4-dihydro-2H-chromene-3,5,7-triol, is shown below:

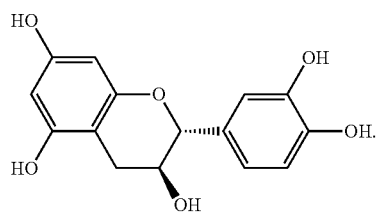 [SMILES: Oc1cc(O)c2c(c1)O[C@H](c1ccc(O)c(O)c1)[C@@H](O)C2]

"Alpha lipoic acid," "thioctic acid," or "6,8-dithiooctanoic acid" has a name of (R)-5-(1,2-dithiolan-3-yl)pentanoic acid and structure of:

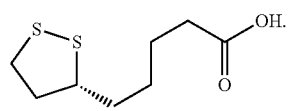 [SMILES: O=C(O)CCCC[C@@H]1CCSS1]

"Dihydrolipoic acid" refers to 6,8-dimercaptooctanoic acid and has the structure of:

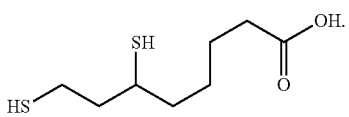 [SMILES: O=C(O)CCCCC(S)CCS]

Examples of amides of alpha lipoic acid include, without limitation, dialkylamine ethylamino lipoate.

"Ubiquinone", also known as "Coenzyme Q10," is a 1,4-benzoquinone, having a name of [(2E,6E,10E,14E,18E,22E,26E,30E,34E)-3,7,11,15,19,23,27,31,35,39-decamethyltetraconta-2,6,10,14,18,22,26,30,34,38-decaenyl]-5,6-dimethoxy-3-methyl cyclohexa-2,5-diene-1,4-dione and structure of:

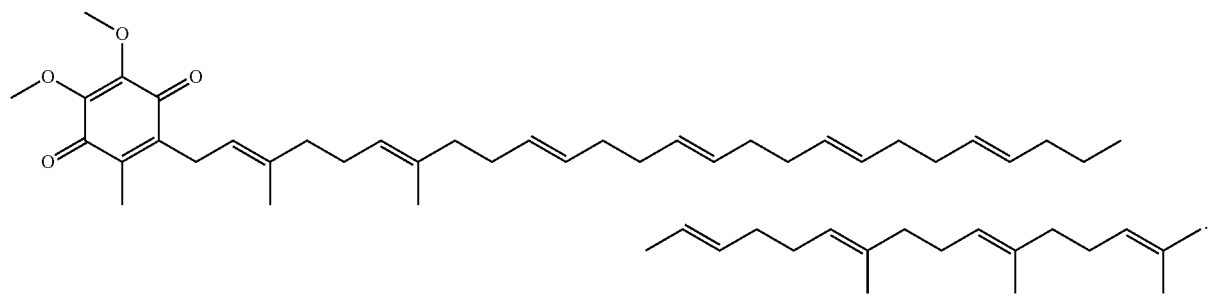

"Ubiquinol" is a fully reduced form of ubiquinone.

Docosahexaenoic acid (DHA) and eicosapentaenoic acid (EPA) are both "omega-3 fatty acids," which refer to unsaturated fatty acids with a double bond (C=C) starting after the third carbon atom from the end of the carbon chain.

DHA has a name of (4Z,7Z,10Z,13Z,16Z,19Z)-docosa-4,7,10,13,16,19-hexaenoic acid

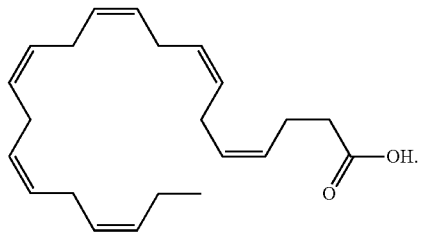 [SMILES: CC/C=C\C/C=C\C/C=C\C/C=C\C/C=C\C/C=C\CCC(=O)O]

EPA has a name of (5Z,8Z,11Z,14Z,17Z)-eicosa-5,8,11,14,17-pentenoic acid and structure of:

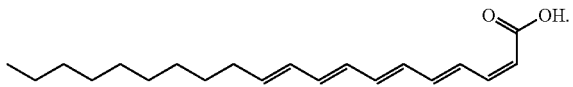 [SMILES: CCCCCCCCC/C=C/C=C/C=C/C=C/C=C\C(=O)O]

In one embodiment, the composition further comprises a vitamin selected from vitamin A, vitamin B, vitamin C, vitamin D, vitamin E, or combinations thereof.

In another embodiment, the composition further comprises minerals such as zinc and magnesium. The minerals can be in the form of oxide or other salt forms.

Another embodiment of the present disclosure provides a composition consisting essentially of (a) a polyphenolic compound, (b) an alpha lipoic acid, a dihydrolipoic acid, or a salt or amide thereof, (c) docosahexaenoic acid (DHA) or an ethyl ester thereof and/or eicosapentaenoic acid (EPA) or an ethyl ester thereof and (d) ubiquinone or ubiquinol. In one aspect, the composition further comprises a vitamin, a mineral or the combination thereof.

The transitional phrase "consisting essentially of," as used herein, intends to exclude ingredients that would materially alter the basic characteristics of the composition. In one aspect, the basic characteristics of the composition include the composition's bioavailability or lack of toxicity. In another aspect, the basic characteristics of the composition include that at least part of the composition is able to cross the blood-retinal barrier (BRB). In one aspect, the composition does not include a substantial portion of plant extracts such as those from blackcurent, bilberry, garlic, curcumin, basil, black pepper and coconut. In one aspect, the composition does not include a substantial portion of whole food blend including that of tomato, broccoli, cabbage, spinach (or octacosanol) and carrot. In one aspect, the composition does not include a substantial portion of red yeast rice, arginine, L-tyrosine, biotin, choline, inositol, Methylsulfonylmethane (MSM), para-aminobenzoic acid (PABA), hyaluronic acid, iodine or its salt forms. As used here, less than a substantial portion of a composition refers to less than about 50%, or alternatively about 40%, 30%, 25%, 20%, 15%, 10%, 9%, 8%, 7%, 6%, 5%, 4%, 3%, 2%, 1%, 0.5%, 0.1% or 0.01% (w/w) of the composition.

In one embodiment, the composition further comprises a pharmaceutically acceptable carrier. As used herein, a "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

In a particular embodiment, the composition comprises:
about 25-800 mg of (a) a polyphenolic compound such as proanthrocyanidins;
about 25-1800 mg of (b) an alpha lipoic acid, a dihydrolipoic acid, or a salt or amide thereof,
about 100-2000 mg of (c) docosahexaenoic acid (DHA) or an ethyl ester thereof and/or eicosapentaenoic acid (EPA) or an ethyl ester thereof, combined, and
about 20-1000 mg of (d) ubiquinone or ubiquinol.

In one aspect, the amount of (a) a polyphenolic compound, e.g., proanthrocyanidins are about 25-200 mg, about 25-300 mg, about 25-400 mg, about 25-800 mg, about 30-200 mg, about 30-300 mg, about 30-400 mg, about 30-800 mg, about 40-150 mg, about 40-300 mg, about 40-400 mg, about 40-800 mg, about 50-200 mg, about 50-300 mg, about 50-400 mg, about 50-800 mg, about 60-200 mg, about 60-300 mg, about 60-400 mg, about 65-400 mg, about 65-800 mg, about 70-400 mg, about 70-800 mg, about 80-200 mg, about 80-300 mg, about 80-400 mg, about 80-800 mg, about 100-800 mg, or about 100-400 mg.

In one aspect, the amount of (b) an alpha lipoic acid, a dihydrolipoic acid, or a salt or amide thereof is about 25-1800 mg, about 25-1500 mg, about 25-800 mg, about 25-600 mg, about 25-500 mg, about 25-300 mg, about 30-1800 mg, about 30-1600 mg, about 30-1200 mg, about 30-300 mg, about 30-800 mg, about 30-700 mg, about 30-600 mg, about 30-500 mg, about 50-300 mg, about 50-1800 mg, about 100-300 mg, about 100-1800 mg, about 150-300 mg, about 150-600 mg, about 150-800 mg, about 150-1800 mg, about 200-600 mg, about 200-800 mg, about 200-1000 mg, about 200-1800 mg, about 250-1800 mg, about 250-600 mg, about 250-1000 mg, about 300-600 mg, about 300-1800 mg, about 300-1500 mg, about 350-1800 mg, about 400-1800 mg, about 450-1800 mg, about 500-1800 mg, about 550-1800 mg, or about 600-1800 mg.

In still another aspect, the amount of (c) docosahexaenoic acid (DHA) or an ethyl ester thereof and eicosapentaenoic acid (EPA) or an ethyl ester thereof, combined is about 100-1500 mg, about 200-1900 mg, about 300-1800 mg, about 400-1700 mg, about 400-1500 mg, about 500-1500 mg, about 600-1600 mg, about 700-1500 mg, about 800-1500 mg, about 800-2000 mg, or about 1000-2000 mg.

In one aspect, the amount of (d) ubiquinone or ubiquinol is about 20-1000 mg, about 35-700 mg, about 35-1000 mg, about 40-600 mg, about 40-500 mg, about 50-400 mg, about 50-300 mg, about 50-1000 mg, about 60-1000 mg, about 60-800 mg, about 80-800 mg, about 80-200 mg, about 80-300 mg, about 80-600 mg, about 100-250 mg, about 100-300 mg, about 100-800 mg, about 150-1000 mg, about 150-800 mg, about 200-1000 mg, about 220-800 mg, or about 250-1000 mg.

In another embodiment, the composition comprises:
about 30-200 mg of (a) a polyphenolic compound;
about 30-400 mg of (b) an alpha lipoic acid, a dihydrolipoic acid, or a salt or amide thereof,
about 500-1500 mg of (c) docosahexaenoic acid (DHA) or an ethyl ester thereof and eicosapentaenoic acid (EPA) or an ethyl ester thereof, combined, and
about 50-300 mg of (d) ubiquinone or ubiquinol.

In one embodiment, the composition comprises:
about 25-800 mg proanthocyanidin,
about 25-1800 mg alpha lipoic acid,
about 100-2000 mg DHA and EPA combined, and
about 20-1000 mg ubiquinone.

In one embodiment, the composition comprises:
about 30-200 mg proanthocyanidin,
about 30-400 mg alpha lipoic acid,
about 500-1500 mg DHA and EPA combined, and
about 50-300 mg ubiquinone.

In any of the above embodiments, the composition further comprises at least one of:
up to about 1000 IU vitamin A,
up to about 1000 mg vitamin B,
up to about 2000 mg vitamin C,
up to about 5000 IU vitamin D,
up to about 800 IU vitamin E,
up to about 40 mg equivalent of zinc, or
up to about 900 mg equivalent of magnesium.

In one embodiment, the composition comprises:
about 0.4%-75% (w/w) proanthocyanidin,
about 0.6%-93% (w/w) alpha lipoic acid,
about 0.6%-97% (w/w) DHA and EPA combined, and
about 0.15%-87% (w/w) ubiquinone.

In another embodiment, the composition comprises:
about 2%-65% (w/w) proanthocyanidin,
about 2%-70% (w/w) alpha lipoic acid,
about 10%-60% (w/w) DHA and EPA combined, and
about 2%-45% (w/w) ubiquinone.

In another embodiment, the composition comprises:
about 2%-55% (w/w) proanthocyanidin,
about 2%-70% (w/w) alpha lipoic acid,
about 15%-50% (w/w) DHA and EPA combined, and
about 0.5%-40% (w/w) ubiquinone.

In another embodiment, the composition comprises:
about 3%-60% (w/w) proanthocyanidin,
about 3%-70% (w/w) alpha lipoic acid,
about 1%-50% (w/w) DHA and EPA combined, and
about 0.2%-40% (w/w) ubiquinone.

In another embodiment, the composition comprises:
about 4%-60% (w/w) proanthocyanidin,
about 4%-70% (w/w) alpha lipoic acid,
about 1%-50% (w/w) DHA and EPA combined, and
about 0.2%-30% ubiquinone.

In another embodiment, the composition comprises:
about 5%-60% (w/w) proanthocyanidin,
about 5%-70% (w/w) alpha lipoic acid,
about 1%-50% (w/w) DHA and EPA combined, and
about 0.2%-25% (w/w) ubiquinone.

In yet embodiment, the composition comprises:
about 10%-60% (w/w) proanthocyanidin,
about 10%-70% (w/w) alpha lipoic acid,
about 5%-45% (w/w) DHA and EPA combined, and
about 0.2%-25% (w/w) ubiquinone.

In still another embodiment, the composition comprises:
about 15%-60% (w/w) proanthocyanidin,
about 15%-70% (w/w) alpha lipoic acid,
about 5%-45% (w/w) DHA and EPA combined, and
about 0.2%-25% (w/w) ubiquinone.

In one embodiment, the composition comprises:
about 20%-60% (w/w) proanthocyanidin,
about 10%-70% (w/w) alpha lipoic acid,
about 1%-30% (w/w) DHA and EPA combined, and
about 0.2%-25% (w/w) ubiquinone.

In one embodiment, the composition comprises:
about 10%-60% (w/w) proanthocyanidin,
about 20%-60% (w/w) alpha lipoic acid,
about 5%-30% (w/w) DHA and EPA combined, and
about 0.2%-20% (w/w) ubiquinone.

In another embodiment, the composition comprises:
about 25%-60% (w/w) proanthocyanidin,
about 10%-60% (w/w) alpha lipoic acid,
about 10%-30% (w/w) DHA and EPA combined, and
about 0.2%-20% (w/w) ubiquinone.

In some embodiments, the combination of proanthocyanidins, alpha lipoic acid, DHA and EPA combined, and ubiquinone constitute at least about 10% (w/w), or at least about 15%, 20%, 25%, 30%, 35%, 40%, 45%, 50%, 60%, 70%, 80%, or 90% (w/w) of the composition.

Tables 1 and 2 below provide exemplary compositions and ranges of daily intake amounts of the compositions.

TABLE 1

Exemplary composition ranges of daily intake

| Components: | Exemplary Composition Range: |
|---|---|
| Omega-3 Fatty acids | 500-1500 mg |
| Alpha Lipoic Acid | 30-400 mg |
| Ubiquinone | 50-300 mg |
| Proanthocyanidins | 30-200 mg |
| Vitamin D | 0-1500 IU |
| Vitamin B Complex | 0-800 mg |
| Vitamin C | 0-500 mg |
| Vitamin A | 0-1000 IU |
| Vitamin E | 0-400 IU |
| Zinc Oxide | 0-35 mg |
| Magnesium Oxide | 0-450 mg |

TABLE 2

Representative sample compositions

| Components: | Sample 1 | Sample 2 | Sample 3 | Sample 4 |
|---|---|---|---|---|
| Omega-3 Fatty acids | 800 mg | 600 mg | 500 mg | 1200 mg |
| Alpha Lipoic Acid | 100 mg | 50 mg | 100 mg | 200 mg |
| Ubiquinone | 50 mg | 50 mg | 100 mg | 80 mg |
| Proanthocyanidins | 30 mg | 30 mg | 30 mg | 45 mg |
| Vitamin D3 | 400 IU | * | 1000 IU | 200 IU |
| Vitamin B Complex | 500 mg | * | * | 500 mg |
| Vitamin C | 100 mg | * | * | 400 mg |
| Vitamin A | * | 1000 IU | * | * |
| Vitamin E | 200 IU | * | * | * |
| Zinc Oxide | * | * | 15 mg | 25 mg |
| Magnesium Oxide | * | * | 500 mg | 500 mg |

* That particular component is absent from the composition.

Methods

Methods of using any of the disclosed compositions are also provided. These compositions, as demonstrated herein, are useful for preventing, stabilizing, and/or treating macular edema. Also shown is that these compositions are effective in improving vision acuity, maintaining intraocular pressure, treating glaucoma associated with central retinal vein occlusion (CRVO), slowing down macular degeneration process and/or reducing inflammation.

Thus, in one embodiment, provided is a method of treating macular edema in a patient in need thereof, comprising administering to the patient a therapeutically effective amount of any of the above disclosed compositions. In another embodiment, provided is a method of improving the vision of a macular edema patient, comprising administering to the patient a therapeutically effective amount of any of the above disclosed compositions.

In yet another embodiment, the present disclosure provides a method of reducing inflammation in the eyes of a macular edema patient, comprising administering to the patient a therapeutically effective amount of any of the above disclosed compositions.

In one aspect, the macular edema patient has suffered or suffers from but not limited to diabetes or a retinal vascular disorder. In one aspect, the retinal vascular disorder comprises central retinal vein occlusion (CRVO), branch retinal vein occlusion (BRVO), age related macular degeneration (AMD), glaucoma, or combinations thereof.

In one aspect, the administration comprises a daily dose of:
about 30-200 mg proanthocyanidin,
about 30-400 mg alpha lipoic acid,
about 500-1500 mg DHA and EPA combined, and
about 50-300 mg ubiquinone.

In another aspect, the administration comprises a daily dose of:
about 30-200 mg proanthocyanidin,
about 30-400 mg alpha lipoic acid,
about 500-1500 mg DHA and EPA combined,
about 50-300 mg ubiquinone, and at least one of:
up to about 1000 IU vitamin A,
up to about 800 mg vitamin B,
up to about 1000 mg vitamin C,
up to about 2000 IU vitamin D,
up to about 400 IU vitamin E,
up to about 35 mg equivalent of zinc, or
up to about 450 mg equivalent of magnesium.

In some aspects, the patient is further administered a therapeutically effective amount of an anti-inflammatory agent or its pro-drug, which can be administered orally, intravitreally, topically as an eye drop, as a cream, in a transdermal patch, or as an implant. In one aspect, the patient is further administered an anti-VEGF antibody, which can be administered intravitreally. In one aspect, the individual further receives eye surgical procedures such as laser photocoagulation.

Formulations, Dosages, and Administration Routes and Schedules

In any of above embodiments, the composition is presented in a tablet, a capsule, a liquid, an eye drop, a cream, a transdermal patch or an implant.

The compositions suitable for administration in the invention can be administered to individuals in need thereof orally, intravitreally, topically, transcorneally, transsclerally/conjunctivally, parenterally (e.g., intramuscular), intravenous or subcutaneous injection, intracisternally, intraperitoneally, sublingually, bucally, as an oral spray, or a nasal spray. The compositions can be formulated in dosage forms appropriate for each route of administration.

Tablet or Capsules, for example hard or soft gelatin capsules, containing the components stated in this invention with or without added excipients, may be prepared by known methods and, if desired, provided with enteric coatings in a known manner. The contents of the capsule may be formulated using known methods so as to give sustained release of the active compound. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate, rice powder, and microcrystalline cellulose. In the case of capsules, tablets and pills, the dosage forms may also comprise buffering agents. They may be of a composition that they release the active ingredient(s) only, or preferentially, in a certain part of the intestinal tract, optionally, in a delayed manner. Examples of embedding compositions that can be used include polymeric substances and waxes.

Solid compositions of a similar type may also be employed as fillers in soft and hard filled gelatin capsules using such excipients as lactose or milk sugar as well as high molecular weight polyethylene glycols.

Liquid compositions may also be formulated with methods known in the art.

If desired, the compositions of the present invention can be incorporated into slow release or targeted delivery systems such as polymer matrices, liposomes and microspheres. They may be sterilized, for example, by filtration through a bacteria-retaining filter, or by incorporating sterilizing agents in the form of sterile solid compositions that can dissolve in sterile water, or some other sterile injectable medium immediately before use.

The composition may be formulated into granules with or without additional excipients. The granules may be ingested directly by the patient or they may be added to a suitable liquid carrier (for example, water) before ingestion. The granules may contain disintegrates, e.g. an effervescent couple formed from an acid and a carbonate or bicarbonate salt to facilitate dispersion in the liquid medium.

The composition may be formulated into a combination of the dosage forms mentioned above.

While there is described herein certain specific embodiments of the present invention, it will be manifest to those skilled in the art that various modifications may be made without departing from the spirit and scope of the underlying inventive concept and that the same is not limited to the particular forms herein described except insofar as indicated by the scope of the claims.

The pharmaceutical compositions can be administered by any one of the following routes: ocular, oral, systemic (e.g., transdermal, intranasal or by suppository), or parenteral (e.g., intramuscular, intravenous or subcutaneous) administration. In some embodiments, the manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another manner for administering compounds of described herein is inhalation.

The choice of formulation depends on various factors such as the mode of key ingredients administration and bioavailability of the key ingredients. For delivery via inhalation the ingredients can be formulated as liquid solution, suspensions, aerosol propellants or dry powder and loaded into a suitable dispenser for administration. There are several types of pharmaceutical inhalation devices-nebulizer inhalers, metered dose inhalers (MDI), mouth mask and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI can dispense therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

The compositions can additional contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols.

Various delivery systems are known and can be used to administer a composition of the invention, e.g., intranasally or by inhalation, and the like. To determine patients that can be beneficially treated, a tissue sample can be removed from the patient and the cells are assayed for sensitivity to the agent.

Therapeutic amounts can be empirically determined and will vary with the pathology being treated, the subject being treated and the efficacy and toxicity of the composition as well as whether the composition is used alone or in combination with other agents of therapeutic methods. When delivered to an animal, the method is useful to further confirm efficacy of the agent.

Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician.

The pharmaceutical compositions can be administered orally, intranasally, ocularly, parenterally or by inhalation therapy, and may take the form of tablets, lozenges, granules, capsules, pills, ampoules, suppositories or aerosol form. They may also take the form of suspensions, solutions and emulsions of the key ingredients in aqueous or nonaqueous diluents, syrups, granulates or powders. In addition to an agent of the present invention, the pharmaceutical compositions can also contain other pharmaceutically active compounds or a plurality of compounds.

More particularly, the composition of the invention also referred to herein as the active ingredient, may be administered for therapy by any suitable route including oral, nasal, topical (including transdermal, aerosol, buccal and sublingual), parenteral (including subcutaneous, intramuscular, intravenous and intradermal) and pulmonary. It will also be appreciated that the preferred route will vary with the condition and age of the recipient, and the disease being treated.

Transdermal delivery systems manufactured as an adhesive disc or patch which slowly releases the compositions described herein for percutaneous absorption can be used. To this end, permeation enhancers can be used to facilitate transdermal penetration of the therapeutic agent. Suitable transdermal patches are described in, for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Use of Compositions for Preparing Medicaments

The compositions of the present invention are also useful in the preparation of medicaments to treat macular edema as described above. The methods and techniques for preparing medicaments of a composition are known in the art.

Thus, one of skill in the art would readily appreciate that any one or more of the compositions described above, including the many specific embodiments, can be used by applying standard pharmaceutical manufacturing procedures to prepare medicaments to treat the many disorders described herein. Such medicaments can be delivered to the subject by using delivery methods known in the pharmaceutical arts.

The following examples are intended to illustrate, but not limit, the invention.

EXAMPLE 1

A 67 year old female patient experienced central vein occlusion in her left eye and subsequently suffered macular edema in 2005. Weak drusens were found in both of her eyes. Her blood results showed that she had higher than normal levels of low-density lipoprotein (LDL), sugar and triglycerides at the time the incident occurred.

The patient received corsteroid injection in the left eye. The macular edema went away for four months. However, the left eye pressure went up to 35-40 mmHg. Eye drops for lowering eye pressure were used to treat the high eye pressure. Within half a year, the patient developed cataract in her left eye and shortly thereafter advanced to a point that her left eye lost most vision and the eye specialist recommended surgery to remove the cataract.

At the time of the surgery, it was discovered that the patient's macular edema had come back and it was rather severe. Avastin injection was then employed to treat macular edema. The edema went away for a month but still came back 2-3 months afterwards. At this point, the patient was notified that regular injection would be required for the rest of her life. As shown in the images from Optical Coherence Tomography (OCT) (FIG. 1), macular edema returned three months after the Avastin injection. Such was a repeated phenomenon since 2005, for more than three years. Macular edema re-occurred typically 3 months following Avastin injection.

In October 2009, the patient started to receive oral administration of the composition of Sample 3 as indicated in Table 2. The administration was once a day for four months.

Significant improvement of vision was observed and the macular edema had not returned at the end of the treatment with Sample 3. The patient continued to take the composition of Sample 3 without other treatments. By January 2011, macular edema had still not recurred after over a year of no Avastin treatment. The patient maintained normal eye pressure of below 10 mmHg. Furthermore, her vision acuity has also improved to be 20/20 compared to 20/40 at the time of diagnosis in 2005.

Figure 2:
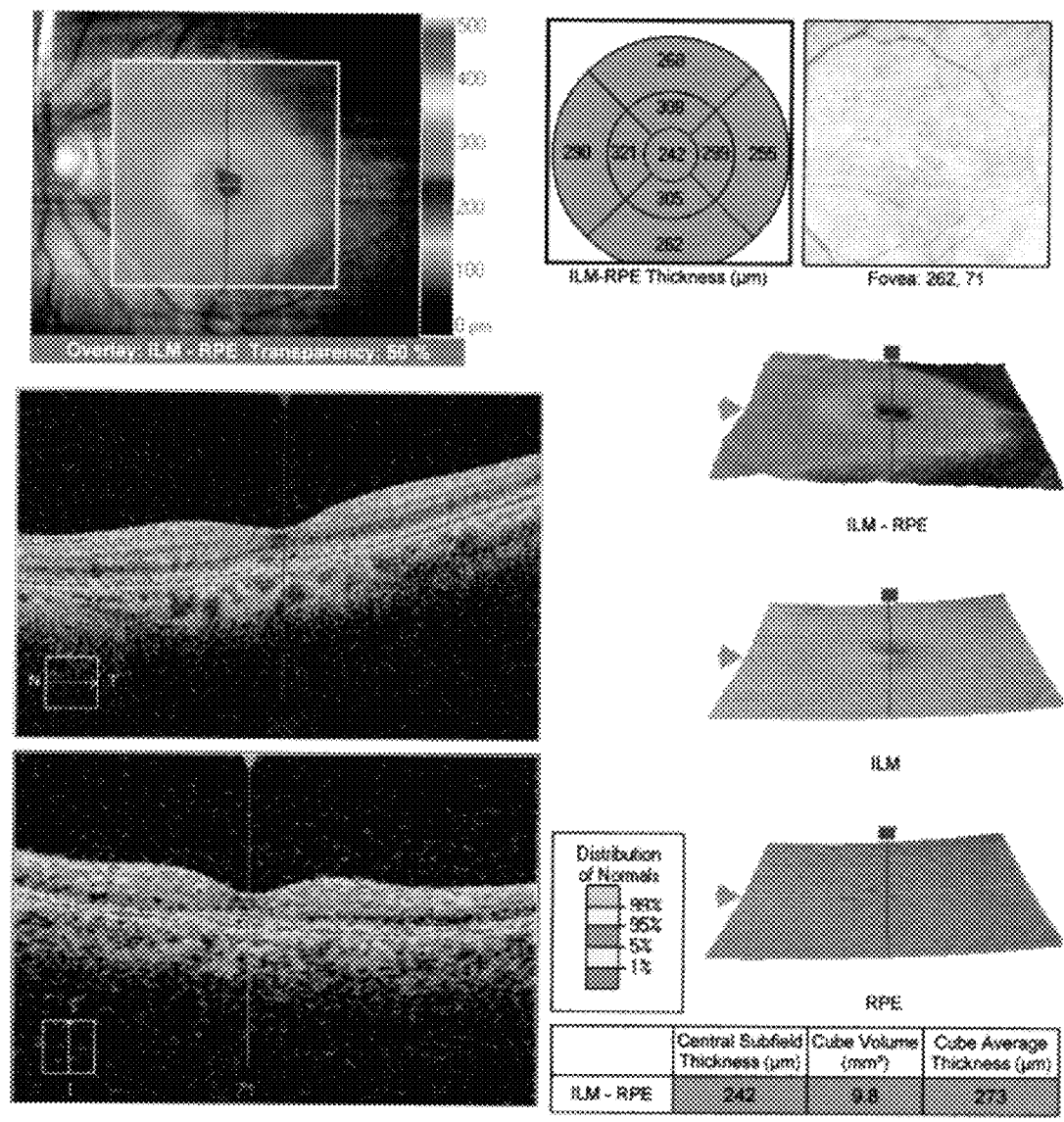
FIG. 2 shows OCT images taken in January 2011 during the patient's regular visit, after the patient was treated with the methods of the present disclosure. As shown in the picture, no macular edema was observed. Up to this time, no Avastin injection was needed for close to two years since the patient received the present technology orally once a day. The vision acuity was 20/20 and the ocular pressure was 9 mmHg.

The eye surgeon was surprised with these testing results. The patient's macular edema was considered to be cured. FIG. 2 is an OCT picture taken in January 2011. As shown in the figure, no macular edema was observed.

EXAMPLE 2

A 89 years old female patient was diagnosed with type II diabetes when she was 70 years old. The patient was advised to improve her diet and lower sugar intake. She started to experience significant vision loss in 2009. In 2009, diabetic macular edema was observed in both eyes. Due to the disease, straight lines appeared wavy. The patient's blood results showed normal levels of LDL and triglycerides. The blood pressure was also normal. The patient began to take the composition of Sample 3 of Table 2 at the beginning of 2010. After three months of daily administration, the macular edema was significantly reduced and the vision acuity had also improved.

EXAMPLE 3

A 78 year old male patient was diagnosed with the wet form of macular degeneration in March 2005. At the time of diagnosis, macular edema was observed. The patient received transpupillary Thermotherapy (TTT) shortly after the diagnosis. In 2010, the patient started to take the composition of Sample 4 of Table 2, daily for four months. Fluorescein angiography examination showed that the macular edema was significantly reduced and the patient's vision acuity improved as well, following the treatment.

EXAMPLE 4

A 79 year old female patient, having cataract in the left eye, received cataract surgery at the beginning of 2011. Macular edema remained after the surgical procedure and the patient's vision acuity was only 20/160. The patient received oral administration of the composition of Sample 1 of Table 2, once a day for two months. It was then found that the patient's macular edema disappeared and her left eye vision acuity improved to 20/20.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

The invention claimed is:

1. A method of treating macular edema in a patient in need thereof, comprising orally administering to the patient a daily dose of a combination of components that consist essentially of:
   about 30-200 mg proanthocyanidin;
   about 30-400 mg alpha lipoic acid;
   about 500-1500 mg docosahexaenoic acid (DHA) and eicosapentaenoic acid (EHA) combined; and
   about 50-300 mg ubiquinone,
   wherein the combination does not contain a substantial portion of plant extracts.

2. The method of claim 1, wherein the macular edema patient has suffered or suffers from diabetes, an ocular disease or retinal vascular disorder or has received an eye surgical procedure.

3. The method of claim 2, wherein the retinal vascular disorder comprises central retinal vein occlusion (CRVO), branch retinal vein occlusion (BRVO), age related macular degeneration (AMD), glaucoma, or combinations thereof.

4. The method of claim 1, further comprising administering to the patient a therapeutically effective amount of an anti-inflammatory agent.

5. The method of claim 1, further comprising administering to the patient an anti-VEGF antibody.

6. The method of claim 1, further comprising treating the patient with laser photocoagulation.

7. The method of claim 1, wherein the combination of components consists essentially of:
   about 30-200 mg proanthocyanidin;
   about 50-300 mg alpha lipoic acid;
   about 500-1500 mg docosahexaenoic acid (DHA) and eicosapentaenoic acid (EPA) combined; and
   about 50-300 mg ubiquinone.

8. The method of claim 1, wherein the combination of components consists essentially of:
   about 30-200 mg proanthocyanidin;
   about 50-300 mg alpha lipoic acid;

about 500-1500 mg docosahexaenoic acid (DHA) and eicosapentaenoic acid (EHA) combined; and about 50-300 mg ubiquinone.

9. The method of claim 1, wherein the combination contains less than about 10% (w/w) plant extracts.

10. The method of claim 9, wherein the combination contains less than about 5% (w/w) plant extracts.

11. The method of claim 1, wherein the combination does not contain a substantial portion of Grape Seed Extract.

12. A method of treating macular edema in a patient in need thereof, comprising orally administering to the patient a daily dose of a combination of components that consists essentially of:
about 30-200 mg proanthocyanidin,
about 30-400 mg alpha lipoic acid,
about 500-1500 mg DHA and EPA combined,
about 50-300 mg ubiquinone,
up to about 1000 IU vitamin A,
up to about 1000 mg vitamin B,
up to about 2000 mg vitamin C,
up to about 5000 IU vitamin D,
up to about 800 IU vitamin E,
up to about 50 mg equivalent of zinc, and
up to about 900 mg equivalent of magnesium,
wherein the combination does not contain a substantial portion of plant extracts.

13. The method of claim 12, wherein the combination contains less than about 10% (w/w) plant extracts.

14. The method of claim 13, wherein the combination contains less than about 5% (w/w) plant extracts.

15. The method of claim 12, wherein the combination does not contain a substantial portion of Grape Seed Extract.

16. A method of improving the vision acuity of a macular edema patient, comprising orally administering to the patient a daily dose of a combination of components that consists essentially of:
about 30-200 mg proanthocyanidin;
about 30-400 mg alpha lipoic acid;
about 500-1500 mg docosahexaenoic acid (DHA) and eicosapentaenoic acid (EPA) combined; and
about 50-300 mg ubiquinone,
wherein the combination does not contain a substantial portion of plant extracts.

17. The method of claim 16, wherein the combination contains less than about 10% (w/w) plant extracts.

18. The method of claim 17, wherein the combination contains less than about 5% (w/w) plant extracts.

19. The method of claim 16, wherein the combination does not contain a substantial portion of Grape Seed Extract.

* * * * *